US006555141B1

(12) United States Patent
Corson et al.

(10) Patent No.: US 6,555,141 B1
(45) Date of Patent: *Apr. 29, 2003

(54) L-ERGOTHIONEINE, MILK THISTLE, AND S-ADENOSYLMETHIONINE FOR THE PREVENTION, TREATMENT AND REPAIR OF LIVER DAMAGE

(75) Inventors: Barbara E. Corson, Fawn Grove, PA (US); Todd R. Henderson, Jarrettsville, MA (US)

(73) Assignee: Nutramax Laboratories, Inc., Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 102 days.

(21) Appl. No.: 09/256,352

(22) Filed: Feb. 24, 1999

Related U.S. Application Data

(60) Provisional application No. 60/076,347, filed on Feb. 27, 1998.

(51) Int. Cl.[7] .............................................. A61K 35/78
(52) U.S. Cl. .................... 424/725; 514/46; 514/398; 514/399
(58) Field of Search ...................... 424/195.1; 514/46, 514/399, 398

(56) References Cited

U.S. PATENT DOCUMENTS

| 3,882,228 A | 5/1975 | Boncey et al. ................. 424/35 |
| 3,887,700 A | 6/1975 | Boncey et al. ................. 424/44 |
| 4,061,765 A | 12/1977 | Madaus et al. ............. 424/278 |
| 4,100,160 A | 7/1978 | Walser ........................ 424/274 |
| 4,296,127 A | 10/1981 | Walser ........................ 424/319 |
| 4,314,989 A | 2/1982 | Rosen .......................... 424/10 |
| 4,994,457 A | 2/1991 | Crawford et al. ........ 514/226.5 |
| 5,084,482 A | 1/1992 | Hirsch et al. ............... 514/562 |
| 5,137,712 A | 8/1992 | Kask et al. ................... 424/10 |
| 5,288,503 A | 2/1994 | Wood et al. ................. 424/497 |
| 5,474,757 A | 12/1995 | Yang .......................... 514/562 |
| 5,569,458 A | 10/1996 | Greenberg ............... 424/195.1 |

OTHER PUBLICATIONS

*The Merck Index*, Budavan et al, eds., Merck & Co., Rahway, New Jersey pp. 26, 1350, 1351, 1989.
Kawano et al, Chem. Pharm. Bull. 31(5):1676–1681, 1983.
Brummel, M.C.: In Search of a Physiological Function for L–Ergothioneine II. Medical Hypotheses 30, 39–48 (1989).
Vogel, Guenter, et al.: Protection by Silibinin against Amanita phalloides Intoxication in Beagles. Toxicology and Applied Pharmacology 73, 355–362 (1984).
Kawano, H. et al.: Studies on Ergothioneine. Chem. Pharm. Bull. 31: 1676–1681 (1983).

Aruoma, Okezie, et al., "Antioxidant Action of Ergothioneine: Assessment of Its Ability to Scavenge Peroxynitrite," Biochemical and Biophysical Research Communication, 231: 389–391 (1997).
Vendemaile, E. et al., "Effects of Oral S–Adenosyl–L–Methionine on Hepatic Glutathione in Patients with Liver Disease," Scand. J. Gastroenterol., 24:407–415 (1989).
Garcea, R. et al., "Inhibition of Promotion and Persistent Nodule Growth by S–Adenosyl–L–Methionine in Rat Liver Carcinogenesis: Role of Remodeling and Apoptosis," Cancer Research, 49:1850–1856 (1989).
Giulidori, P. et al., "Transmethylation, Transsulfuration and Aminopropylation Reactions of S–Adenosyl–L–Methionine in Vivo," J. Biol. Chem., 259:4205–4211 (1984).
Feo, F. et al., "The Variations of S–adenosyl–L–methionine Content Modulate Hepatocyte Growth During Phenobarbital Promotion of Diethylnitrosamine–Induced Rat Liver Carcinogenesis," Toxicol. Pathol. 15:109–114 (1987).
Adachi, Y., et al., The Effects of S–adenosylmethionine on Intrahepatic Cholestasis, Japan Arch. Inter. Med., 33(6), pp. 185–192 (1986).
Akanmu, D., et al., The antioxidant action of ergothioneine, Arch. of Biochemistry and Biophysics, 288(1), pp. 10–16 (1991).
Baldessarini, F., Neuropharmacology of S–Adenosyl Methionine, American Journal of Medicine 83 (5A), p. 95 (1987).
Devi B., et al., Protection of rat fetal hepatocytes membranes from ethanol mediated cell injury and growth impairment, Hepatology 16, p. 109A (1992).
Carney, M., Neuropharmacology of S–Adenosyl Methionine, Clinical Neuropharmacology 9(3), p. 235 (1986).
Champ, P. and Harvey, R., Biochemistry, 2nd ed., Lippincott, Philadelphia, pp. 266–267 (1994).
Conti, M., et al., Protective activity of Silipide on liver damage in rodents, Japan J. Pharmacol., 60, pp. 315–321 (1992).
Feo F., et al., Early Stimulation of Polyamine Biosynthesis During Promotion by Phenobarbital of Diethylnitrosamine–induced Rat Liver Carcinogenesis. The Effects of Variations of the S–adenosyl–L–methionine Cellular Pool, Carcinogenesis, 6 (12), pp. 1713–1720 (1985).
Foster, S., A Field Guide to Medicinal Plants, Houghton Miffing Co., Boston, p. 198 (1990).

(List continued on next page.)

Primary Examiner—Francisco Prats

(57) ABSTRACT

This invention provides therapeutic compositions for the protection, treatment and repair of liver tissue. The invention relates to novel compositions comprising two or more compounds selected from the group consisting of S-adenosylmethionine, L-ergothioneine, and a compound selected from the group consisting of Milk thistle (*Silybum marianum*), silymarin and active components of silymarin, whether naturally, synthetically, or semi-synthetically derived, and to methods of preventing and treating liver disease and of repairing damaged liver tissue. The invention also provides a method of administering these compositions to humans or animals in need thereof.

16 Claims, 6 Drawing Sheets

OTHER PUBLICATIONS

Frezza, M., The use of SAMe in the treatment of cholestatic disorders, Drug Investigation, 4 (Suppl. 4), pp. 101–108 (1992).

Garcea, R., et al., Variations of Ornithine Decarboxylase Activity ad S–adenosyl–L–methionine and 5'–methylthioadenosine Contents During the Development of Diethylnitrosamine–induced Liver Hyperplastic Nodules and Hepatocellular Carcinoma, Carcinogenesis, 8 (5), pp. 653–658 (1987).

Hanlon, D., Interactions of ergothioneine with metal ions and metalloenzymes, J. Med. Chem., 14 (11), pp. 1084–1087 (1971).

Janicak, P., S–Adenosylmethionine in Depression, Alabama Journal of Medical Sciences 25 (3), p. 306 (1988).

Kawano, H., et al., Studies on Ergothioneine: Inhibitory effect on lipid peroxide formation in mouse liver, Chem. Pharm. Bull., 31 (5), pp. 1662–1687 (1983).

Lieber, C., Biochemical factors in alcoholic liver disease, Seminars in Liver Disease, 13 (2), pp. 136–153 (1993).

Parish, R. & Doering, P., Treatment of Amanita mushroom poisoning: a review, Vet. Hum. Toxocol., 28 (4), pp. 318–322 (1986).

Pascale R., et al., The role of SAMe in the regulation of glutathione pool and acetaldehyde production in acute ethanol intoxication, Research Communications in Substances of Abuse, vol. 5, No. 4, pp. 321–324 (1984).

Pascale, R., et al., Inhibition by ethanol of rat liver plasma membrane (Na+ K+) ATPase: protective effect of SAMe, L–methionine, and N–acetylcysteine, Toxicology and Applied Pharmacology, 97, pp. 216–229 (1989).

Stramentinoli, G., Pharmacologic Aspects of S–Adenosylmethionine, American Journal of Medicine 83 (5A), pp. 35–42 (1987).

Tyler, v., The Honest Herbal, Haworth Press, Inc., New York, pp. 209–210 (1993).

Wichtl, M. (Grainger Bisset, N, trans.), Herbal Drugs and Phytopharmaceuticals, CRC Press, Boca Raton, pp. 121, 124, 125 (1994).

Par, A., "Pathogenesis and Management of Alcoholic Liver Injury",Acta Physiologica Hungarica. Jan. 1992, vol. 80 Nos. 1–4, pp. 325–350, especially pp. 325, 343–344 & 346.

Feo, F, Pirisi L, Garcea R, et al.: The role of phosphatidylethanolamine methylation in the synthesis of phosphatidylcholine in acute ethanol intoxication. Research Communications in Substances of Abuse 1982: 3:499–502.

Pascale R, Garcea R, Daino L, et al.: The role of S–Adenosylmethionine in the regulation of gluthathione pool and acetaldehyde production in acute ethanol intoxication. Research Communications in Substances of Abuse 1984; 5:321–324.

Feo F, Pascale R, Garcea R, et al.: Effect of the variations of S–Adenosyl–L–methionine liver content on fat accumulation and ethanol metabolism in ethanol–intoxicated rats. Toxicology and Applied Pharmacology 1986; 83:331–341.

Paredes Sr, Kozicki PA, Fukuda H. et al.: S–Adenosyl–L–Methionine: its effect on amin olevulinate dehydratase and gluthathione in acute ethanol intoxication. Alcohol 1987; 4:81–85.

Pascale R, Daino L, Garcea R, et al.: Inhibition by ethanol of rat liver plasma membrane (Na+,K+)ATPase: protective effect of S–Adenosyl–L–Methionine, L–Methionine, and N–Acetylcysteine. Toxicology and Applied Pharmacology 1989; 97:216–229.

Lieber CS, Casini A, Decarli LM, et al.: S–Adenosyl–Lmethionine attenuates alcohol–induced liver injury in the baboon. hepatology 1990; 11:165–172.

Vara E, Arias–Diaz J, Garcia C, et al. S–adenosyl–methionine might protect transplanted hepatocytes against the toxic effects of cytokines. Transplantation Proceedings 1994; 26(6):3363–3365.

Chawla RK, Hussain S, Watson WH, et al.: Effect of ethanol consumption on metabolism of S–Adenosyl–L–Methionine in rat liver. Drug Investigation 1992; 4(Suppl.4):41–45.

Devi GB, Henderson GI, Frosto TA, et al.: Effect of ethanol on rat fetal hepatocytes: studies on cell replication, lipid peroxidation and glutathione. Hepatology 1993; 18(3):648–659.

Chawla RK, Jones DP. Abnormal metabolism of S–adenosyl–L–methionine in hypoxic rat liver. Similarities to its abnormal metabolism in alcholic cirrhosis. Biochimica et Biophysica Acta 1994; 1199:45–51.

Seyoum G, Persaud TVN. In vitro effect of s–adenosyl methionine on ethanol embryopathy in the rat. Exp Toxic Pathol 1994;46:177–181.

Alvaro D, Gigliozzi A, Piat C, et al. S–adenosylmethionine (SAMe) protects against acute ethanol hepatotoxicity in the isolated perfused rat liver (IPRL) with no effect on trascytosis. EASL, Journal of Hepatology 1994;21(Suppl 1):S81.

Di Padova C, Tritapepe R, Rovagnati P, et al.: Decreased blood levels of ethanol and acetaldehyde by S–Adenosyl–L-Methionine in humans. Archives of Toxicology 1984; (Suppl.7):240–242.

Cibin M, Gentile N, Ferri M, et al.: S–Adenosylmethionine (SAMe) is effective in reducing ethanol abuse in an outpatient program for alcoholics. Biochemical and social aspects of alcohol and alcoholism. In: Kuriyama K, Takada A, Ishii H(Eds). Elsevier Science Publishers. 1988; pp. 357–360.

Vendemiale G, Altomare E, Trizio T, et al.: Effects of oral S–Adenosyl–L–Methionine on hepatic glutathione in patients with liver disease. Scandanavian Journal of Gastroenterology 1989; 24:407–415.

Caballeria E, Moreno J: Therapeutic effects of S–Adenosylmethionine (SAMe) in hepatic steatosis. A pilot study. Acta Therapeutica 1990; 16:253–264.

Loguercio C, Nardi G, Argenziio F, et al. Effect of s–adenosyul–L–methionine administration on red blood cell cysteine and glutathione levels in alcoholic patients with and without liver disease. Alcohol & Alcoholism 1994;29(5):597–604.

Lieber CS: Alcoholic liver injury. Current Opinion in Gastroenterology 1992; 8:449–457.

Lieber CS: Hepatotoxicity of alcohol. Implications for the therapy of alcoholic liver disease. Drug Investigation 1992; 4(Suppl.4):1–7.

Lieber CS, Decarli LM: Hepatotoxicity of ethanol. Journal of Hepatology 1991; 12;394–401.

Israel Y, Speisky H, Lanca AJ, et al. Metabolism of hepatic glutathione and its relevance in alcohol induced liver damage. In: Cellular and Molecular Aspects of Cirrhosis. Clement B, Guillouzo A (Eds). Colloque INSERM, John Libbey Eurotext Ltd. 1992; 216:pp. 25–37.

Dunne B, Davenport M, Tredger JM, et al.: Evidence that S–adenosylmethionine and N–Acetylcysteine reduce in injury from sequential cold and warm ischaemia in the isolated perfused rat liver. Transplantation 1994; 57:1161–1168.

Schenker S, Halff Ga. Nutritional therapy in alcoholic liver disease. Seminars in Liver Disease 1993; 13(2):196–209.

Lieber CS. Alcohol and the liver. In: Fat–Storing Cells and Liver Fibrosis. Surrenti C, Casini A, Milani S, et al. (Eds), Kluwer Academic Publishers, Lancaster, UK, 1994; pp. 135–166.

Buchet JP, Guebel A, Pauwels S, et al.: The influence of liver disease on the methylation of arsenite in humans. Archives of Toxicology 1984; 55:151–154.

Gentile S, Persico M, Orlando C, et al.: Effect of different doses of S–adenosyl–L–methionine (SAMe) on nicotinic acid–induced hyperbilirubinaemia in Gilbert's syndrome. Scandinavian Journal of Clinical Laboratory Investigation 1988; 48:525–529.

Geubel AP, Mairlot MC, Buchet JP, et al.: Abnormal methylation capacity in human liver cirrhosis. International Journal of Clinical Pharmacology Research 1988; VIII(2):117–122.

Vendemaile G, Altomare E, Altavilla R, et al.: S–Adenosylmethionine (SAMe) improves acetaminophen metabolism in cirrhotic patients. Journal of Hepatology 1989; 9:S240.

Gentile S, Persico M, Orlando C, et al.: Age–associated decline of hepatic handling of cholephilic anions in humans is reverted by S–adenosylmethionine (SAMe). Scandinavian Journal of Clinical Laboratory Investigation 1990; 50:565–571.

Persico M, Gentile S, Di Padova C: S–Adenosylmethionine (SAMe)—induced improvement of hepatic handling of organic anions in cirrhosis. Gastroenterology 1990; 98:A620.

Kaye GL, Blake JC, Burroughs AK: Metabolism of exogenous S–Adenosyl–L–Methionine in patients with liver disease. Drugs 1990; 40 (Suppl 3):124–128.

Cuomo R, Dattilo M, Pumpo R, et al. Nicotinamide methylation in patients with cirrhosis. Journal of Hepatology 1994; 20:138–142.

Persico M, Romano M, Villano N, et al. The association between rifamycin–SV (R–SV) related hyperbilirubinaemia and antipyrine clearance as a new test of liver function in cirrhosis. European Journal of Clinical Investigation 1994; 24:201–204.

Cuomo R. Pumpo R, Capuano G, et al.S–adenosyl–L–methionine (SAMe)–dependent nicotinamide methylation: a marker of hepatic damage. In: Falk Symposium 71—Fat Storing Cells and Liver Fibrosis. Surrenti C, Casini A, Milani S (Eds), Kluwer Academic Publishers, Lancaster, UK, 1994; pp. 348–353.

Piccinino F, Sagnelli E, Pasquale G, et al.: S–Adenosyl–Methionine in patients with chronic active hepatitis treated with steroids. Italian Journal of Gastroenterology 1982; 14:186–187.

Dunne B, Davenport M, Piratvisuth T, et al.: Donor pretreatment is essential for maximal benefit of S–adenosylmethionine in reducing experimental hepatic ischaemic injury. Hepatology 1993;18(4):64A.

Giannuoli G, Tine' F,Malizia G, et al.: S–Adenosylmethionine for treatment of pruritus in compensated chronic liver disease. A pilot study. Hepatology 1986; 6:1110.

Cacciatore L, Varriale A, Cozzolino g, et al.: S–Adenosylmethionine (SAMe) in the treatment of pruritus in chronic liver disease. Acta Therapeutica 1989; 15:363–371.

Frezza M, Surrenti C, Manzillo G, et al.: Oral S–Adenosylmethionine in the symptomatic treatment of intrahepatic cholestasis. A double–blind, placebo–controlled study. Gastroenterology 1990; 99:211–215.

Botero RC, Delgado C: Placebo controlled trial of intravenous S–Adenosylmethionine (SAMe) in patients with acute hepatitis A, B, and NANB. Hepatology 1991; 14:199A.

Caballero Plasencia AM, Montero Garcia M., Ceballos Torres A., et al.: Total parenteral nutrition plus S–Adenosylmethionine in a case of intrahepatic cholestasis. Drug Investigation 1991; 3:333–335.

Mascio G, De Filippis g, Bortonlini M: Intramuscular (IM) and intravenous (IV) S–Adenosylmethionine 1,4 butanedisfulonate (SAMe SD4) for the symptomatic treatment of intrahepatic cholestasis (IHC). Results of placebo–controlled study. The Italian Journal of Gastroenterology 1991; 23:314–315.

Roda E, Cipolla A, Villanova N, et al. Effects of ademetionine (SAMe) and UDCA on bile acid metabolism and bile acid pool size in primary biliary cirrhosis. In: Falk Symposium 71—Fat–Storing Cells and Liver Fibrosis. Surrenti C, Casini A, Milani (Eds), Kluwer Academic Publishers, Lancaster, UK, 1994; pp. 354–360.

Owen JS, Bruckdorfer KR, Day RC, et al.: Decreased erythrocyte membrane fluidity and altered lipid composition in human liver disease. Journal of Lipdi Research 1982; 23:124–132.

Kakimoto H, Kawata S, Imai Y, et al.: Changes in lipid composition of erythrocyte membranes with administration of S–adenosyl–L–methionine in chronic liver disease. Gastroenterologia Japonica 1992; 27:508–513.

Owen JS, Rafique S, Osman E, et al.: Ability of S–Adenosyl–L–Methionine to ameliorate lipoprotein–induced membrane lipid abnormalities and cellular dysfunctions in human liver disease. Drug Investigation 1992; 4 (suppl. 4):22–40.

Rafique S, guardascione M, Osman E, et al.: reversal of extrahepatic membrane cholesterol deposition in patients with chronic liver diseases by S–adensyl–L–methionine. Clinical Science 1992; 83:353–356.

Laffi G, Foschi M, Carloni V, et al. Plasma membrane abnormalities in chronic liver disease. In: Cholestasis. Gentilini P, Arias IM, McIntyre N, et al., Elsevier Science B.V., Amsterdam, 1994; pp. 205–212.

Bortolini M, Almasio P, Bray G, et al.: Multicentre survey of the prevalence of intrahepatic cholestasis in 2520 consecutive patients with newly diagnosed chronic liver disease. Drug Investigation 1992; 4(suppl.4): 83–89.

Dunne B, Davenport M, Williams R, et al.: Benefit of S–adenosylmethionine after sequential cold and warm hepatic ischaemic is derived from three separate treatment stages. EASL, Journal of Hematology 1993; 18(suppl 1):S66.

Manzillo G, Piccinino f, Surrenti C, et al.,: Multicentre double–blind placebo–controlled study of intravenous and oral S–Adenosyl–L–Methionine (SAMe) in cholestatic patients with liver disease. Drug Investigation 1992; 4 (suppl.4): 90–100.

Bray GP, Tredger M, Williams R: Resolution of danazol–induced cholestasis with S–adenosylmethionine. Postgraduate Medical Journal 1993; 69:237–239.

Iemmolo Rm, fabris L, Strazzabosco M, et al.: Intrahepatic cholestasis in biliary cirrhosis secondary to graft versus host disease (GVHE): report of a case treated with ademetionine (SAMe). Journal of Hepatology 1993, 18:S132.

Rafique S, Guardascione M, Burroughs AK, et al.: S–Adenosylmethionine (SAMe) in the treatment of benign recurrent intrahepatic cholestasis (BRIC). European Journal of Clinical Investigation 1991; 21:30.

Bray GP, Di Padova C, Tredger JM, et al.: A comparison of S–Adenosylmethionine(SAMe), rifampicin (R) and urodeoxycholic acid (UDCA) in primary biliary cirrhosis (PBC): interim results. Journal of Hepatology 1991; 13:S101.

Roda E, Roda A, Le Grazie C: Effect of oral Ademetionine (SAMe) on bile acid (BA) metabolism in primary biliary cirrhosis (PBC). European Journal of clinical Investigation 1992; 22:A19.

Schreiber AJ, Warren G, Sutherland E, et al.: Enhancement of taurocholate secretory maximum: S–Adenosyl Methionine (SAM)–induced cytoprotection. Clinical Research 1983; 31:86A.

Schreiber AJ, Warren G, Sutherland E, et al.: S–Adenosyl Methionine (SAMe)–induced cytoprotection against bile acid–induced cholestasis. Gastroenterology 1983, 84:1395.

Arias IM, Kinne R: On the pathophysiology and reversibility of intrahepatic cholestasis. Clinical Research 1984; 32:548A.

Di Padova C, Di Padova F, tritapepe r, et al.: S–Adenosyl–L–Methionine protection against a–naphthyl–isothiocyanate–induced cholestasis in the rat. Toxicology Letters 1985; 29:131–136.

Nanno T, Adachi Y, Takahashi H, et al.: Effect of S–adenosyl–L–methionine (SAMe) on experimental intrahepatic cholestasis. Proc Jpn Soc Clin Metab 1987; 24.

Cuomo, r. Rodino S, Rizzoli R, et al.: Bile and biliary secretion in rats with hexachlorobenzene–induced prophyria. Effect of S–adenosyl–L–methionine administration. Journal of Hepatology 1991; 12:87–93.

Jimenez R, Munoz Me, Moran D, et al.: Effect of acute preadministration of Sulfoadenosyl–L–Methionine (SAMe) on the hepatotoxicity of cyclosporine A. Hepatology 1992; 16:268A.

Fischer G, Sagesser H, Talos C. et al.: S–Adenosylmethionine (SAMe) does not restore microsomal function in rats with secondary biliary cirrhosis (SBC) but improves trans–sulphuration. Journal of Hepatology 1992; 16:S71.

Gonzalez–Gallego J, Almar MM, Villa JG, et al.: Pretreatment of rats with S–Adenosyl–L–Methionine (SAMe) prevents exercise–induced cholestasis. Journal of Hepatology 1992; 16:S93.

Fernandez E, Munoz ME, Roman ID, et al.: Cyclosporin A–induced cholestasis in the rat. Beneficial effects of S–Adenosyl–L–Methionine. Drug Investigation 1992; 4(Suppl.4):54–63.

Villa JG, Almar MM, Collado PS, et al.: Impairment of bile secretion induced by exhaustive exercise in the rat. Int. J. sports Med. 1983; 14:179–184.

Belli DC, Fournier La, LePage G, et al.: S–adenosylmethionine prevents total parenteral nutrition–induced cholestasis in the rat. Journal of Hepatology 1994; 21:18–23.

Muriel P, Suarez OR, Gonzales P, et al.: Protective effect of S–adenosyl–l–methionine on liver damage induced by biliary obstruction in rats: a histological ultrastructural and biochemical approach. Journal of Hepatology 1994; 21, 95–102.

Stramentinoli G: Modulation of membrane fluidity by S–adenosylmethionine treatment in different experimental conditions. In: 1st Conference on Biochemical Pharmacological and Clinical Aspects of Transmethylation. Mato JM (Ed). Jarpyo Editores, Madrid, 1986, pp. 97–104.

Brown MD, Dideja PK, Brasitus TA: S–Adenosyl–L–methionine modulates Na+ + K+ –ATPase activity in rat colonic basolateral membranes. Biochemical Journal 1988; 251:215–222.

Muriel P, Mourelle M: Prevention and reversion of erythrocyte membrane alterations in cirrhosis by S–adenosylmethionine. Hepatology 1989; 10:742.

Tsuji M. Kodama K, Oguchi K: Protective effects of S–Adenosyl–L–Methionine against enzyme leakage from cultured hepatocytes and hypotonic hemolysis. Japanese Journal of Pharmacology 1990; 52:45–49.

Muriel P, Mourelle M: Characterization of membrane fraction and lipid composition and function of cirrhotic rat liver. Role of S–adenosyl–L–methionine. Journal of Hepatology 1992; 14:16–21.

Stramentinoli G, Gualano M, Ideo G: Protective role of S–Adenosyl–L–Methionine on liver injury induced by D–Galactosamine in rats. Biochemical Pharmacology 1978; 27:1431–1433.

Stramentinoli G, Pezzoli C, Galli–Kienle M: protective role of S–Adenosyl–L–Methionine against acetaminophen induced mortality and hepatotoxicity in mice. Biochemical Pharmacology 1979; 28:3567–3571.

Osada J, Aylagas H, Sanchez–Vegazo I, et al.: Effect of S–Adenosyl–L–Methionine on thioacetamide–induced liver damage in rats. Toxicology Letters 1986; 32:97–106.

Fell D, Stelle Rd: effect of retinol toxicity on hepatic S–Adenosylmethionine–dependent transmethylation in rats. Drug–Nutrient Interactions 1987;5:1–7.

Osada J, Aylagas H, Palicios–Alaiz E: Effects of S–adenosyl–L–methionine on phospholipid methyltransferase activity changes induced by thioacetamide. Biochemical Pharmacology 1990; 40:648–651.

Tsuji M, Kodama K, Oguchi K: Protective effect of S–Adenosyl–L–Methionine against CC14–induced hepatotoxicity in cultured hepatocytes. Japanese Journal of Pharmacology 1990; 52:209–214.

Ponsoda X, Jover R, Gomez–Lechon MJ, et al.: Intracellular glutathione in human hepatocytes incubated with S–Adenosyl–L–methionine and GSH–depleting drugs. Toxicology 1991; 70:293–302.

Bray GP, Tredger JM, Williams R: S–Adenosylmethionine protects against acetaminophen hepatotoxicity in two mouse models. Hepatology 1992; 15:297–301.

Concari M, Guicciardi ME, Carubbi F, et al.,: S–adenosyl–L–methionine (SAMe) reduces hepatotoxicity induced by hydrophobic bile salts (BS) in hepG2 cell line. EASL, Journal of Hepatology 1994, 21 (Suppl 1):S77.

Lucas R, Moran D, Fernandez E, et al.: Ability of S–adenosyl–L–methionine (SAMe) to antagonize cyclosporine A–induced inhibition of the biliary excretion of glutathione. EASL, Journal of Hepatology 1994; 21 (Suppl 1):S87.

Casini A, Banchetti E, Milani S, et al.: S–Adenosylmethionine inhibits collagen synthesis by human fibroblasts in vitro. Methods and Findings Experimental Clinical Pharmacology 1989; 11:331–334.

Cutrin C, Menino Mj, Carballo C, et al.: Lactacidaemia in rats with cirrhosis induced by carbon tetrachloride and ethanol: treatment with colchicine, nifedipine and S–adenosylmethionine. Medical Science Research 1991; 19:351–352.

Corrales F, Gimenez A, Alvarez L, et al.: S–adenosylmethionine treatment prevents carbon tetracholoride–induced S–adenosylmethionine synthetase inactivation and attenuates liver injury. hepatology 1992; 16: 1022–1027.

Cutrin C, Menino MJ, Otero x, et al.: Effect of nifedipine and S–Adenosylmethionine in the liver of rats treated with CC14 and ethanol for one month. Life Sciences 1992; 51:113–118.

Barrio E, Cutrin C, Menino MJ, et al.: Comparative effect of nifedipine and S–adenosylmethionine, singly and in combination on experimental rat liver cirrhosis. Life Sciences 1993; 52:PL 217–220.

Caballeria J, Gimenez A, Corrales F, et al.: Effects of S–adenosylmethionine (SAMe) on experimental liver fibrosis. In: Falk symposium 71. Fat–storing Cells and Liver Fibrosis. Surrenti C, Casini A, Milani S, et al. (Eds). Kluwer Academic Publishers, Lancaster, UK, 1994; pp. 314–321.

Gasso M, Caballeria J, Cabre M, et al.: Influence of S–adenosylmethionine (SAMe) on lipid peroxidation and liver fibrogenesis in CC14–Induced cirrhosis. EASL, Journal of Hepatology 1994;21 (Suppl 1):S3.

Dunne B, Davenport M, Tredger JM, et al.: S–Adenosylmethionine and N–Acetylcysteine in the treatment of experimental ischaemic liver injury. Journal of Hepatology 1992; 16:S46.

Dunne B, Davenport M, Williams R, et al.: S–adenosylmethionine improves hepatic function during liver perfusion after sequential cold and warm ischaemic injury. Submitted to: British Transplant Society, 1992.

Thom H, Bortolini M, Galli–Kienle M: Anti–ischaemic activity of S–Adenosyl–L–Methionine (SAMe) during hypoxia/reoxygenation in the isolated perfused rat liver. Drug Investigation 1992; 4 (Suppl.4):64–68.

Scott PD, Knoop M, McMahon FRT, et al.: S–Adenosyl–L–Methionine protects against haemorrhagic pancreatitis in partially immunosuppressed pancreaticoduodenal transplant recipients. Drug Investigation 1992; 4 (Suppl4):69–77.

Dunne JB, Davenport M, Williams R, et al.: Benefit of S–Adenosylmethionine after sequential cold and warm hepatic ischaemia is derived from three separate treatment stages. Journal of Hepatology 1993; 18:S66.

Dausch, J.G. and Fullerton, F.R., Increased Levels of S–Adenosylmethionine in the Livers of Rats Fed Various Forms of Selenium, Nutrition and Cancer, vol. 20, No. 1, pp. 31–39 (1993).

Hartman, Philip E., Ergothioneine as Antioxidant, Methods in Enzymology, vol., 186, pp. 310–318 (1990).

Baldessarini, F., *Neuropharmacology of S–Adenosyl Methionine*, American Journal of Medicine 83 (5A), p. 95 (1987).

Devi B., et al., Protection of rat fetal hepatocytes membranes from ethanol mediated cell injury and growth impairment, Hepatology 16, p. 109A (1992).

Carney, M., *Neuropharmacology of S–Adenosyl Methionine*, Clinical Neuropharmacology 9(3), p. 235 (1986).

Feo F., et al., *Early Stimulation of Polyamine Biosynthesis During Promotion by Phenobarbital of Diethylnitrosamine–induced Rat Liver Carcinogenesis. The Effects of Variations of the S–adenosyl–L–methionine Cellular Pool*, Carcinogenesis, 6(12), pp. 1713–20 (1985).

Frezza, M., *The use of SAMe in the treatment of cholestatic disorders*, Drug Investigation, 4(Suppl. 4), pp. 101–08 (1992).

Garcea, R., et al., *Variations of Ornithine Decarboxylase Activity ad S–adenosyl–L–methionine and 5'–methylthioadenosine Contents During the Development of Diethylnitrosamine–induced Liver Hyperplastic Nodules and Hepatocellular Carcinoma*, Carcinogenesis, 8(5), pp. 653–58 (1987).

Hanlon, D., *Interaction of ergothioneine with metal ions and metalloenzymes*, J. Med. Chem., 14(11), pp. 1084–87 (1971).

Janicak, P., S–*Adenosylmethionine in Depression*, Alabama Journal of Medical Sciences 25(3), p. 306 (1988).

Kawano, H., et al., *Studies on Ergothioneine: Inhibitory effect on lipid peroxide formation in mouse liver*, Chem. Pharm. Bull., 31(5), pp. 1662–87 (1983).

Lieber, C., *Biochemical factors in alcoholic liver disease*, Seminars in Liver Disease, 13 (2), pp. 136–53 (1993).

Parish, R. & Doering, P., *Treatment of Amanita mushroom poisoning: a review*, Vet. Hum. Toxocol., 28 (4), pp. 318–22 (1986).

Stramentinoli, G., *Pharmacologic Aspects of S–Adenosylmethionine*, American Journal of Medicine 83 (5A), pp. 35–42 (1987).

Tyler, v., The Honest Herbal, Haworth Press, Inc., New York, pp. 209–10 (1993).

Par, A., "Pathogenesis and Management of Alcoholic Liver Injury", Acta Physiologica Hungarcia. Jan. 1992, vol. 80 Nos. 1–4, pp. 325–350, especially pp. 325, 343–344 & 346.

S-ADENOSYLMETHIONINE

L-ERGOTHIONEINE

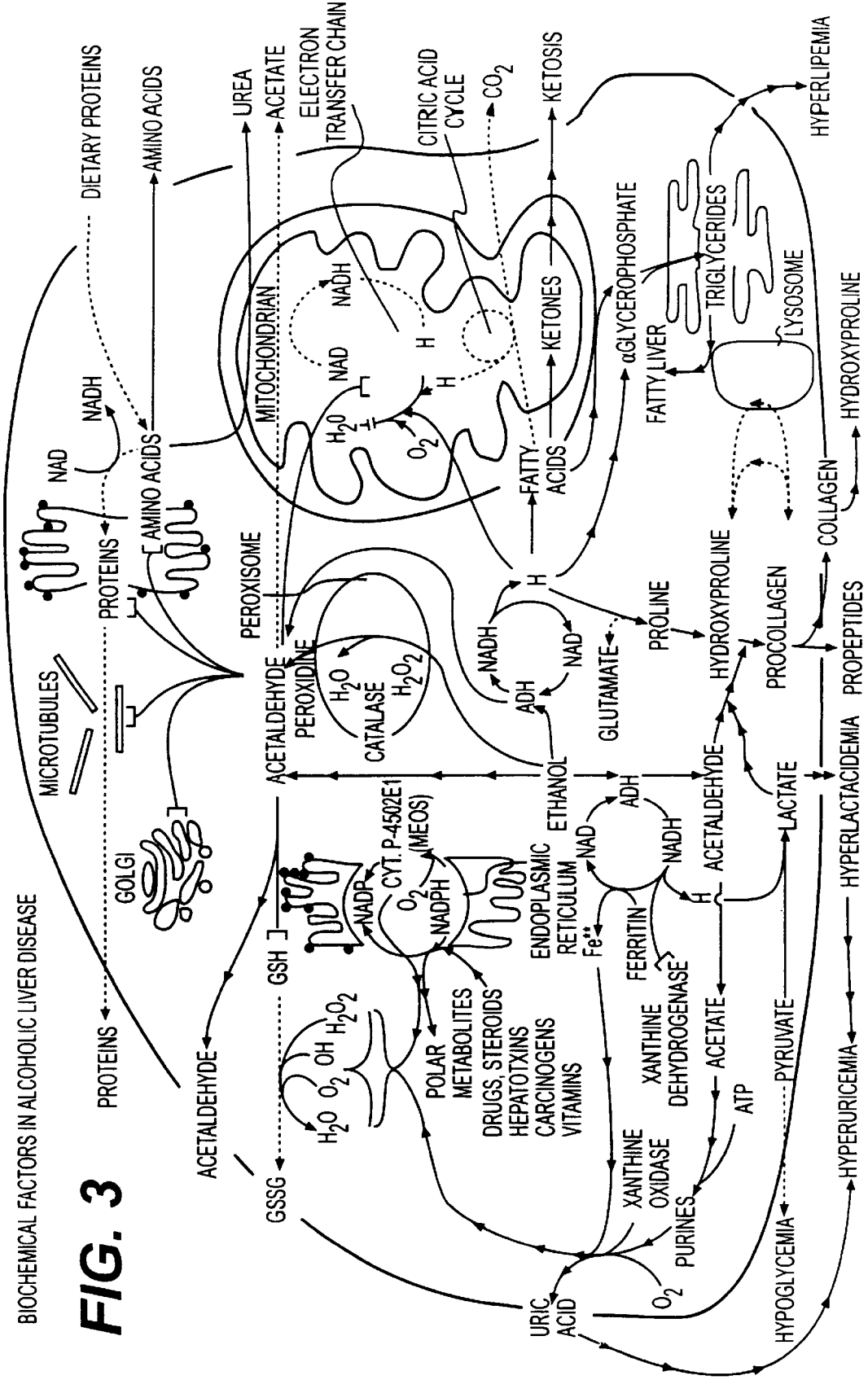
FIG. 3 BIOCHEMICAL FACTORS IN ALCOHOLIC LIVER DISEASE

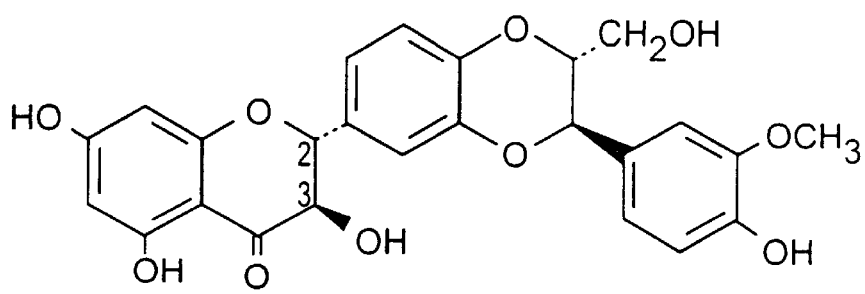
SILYBIN
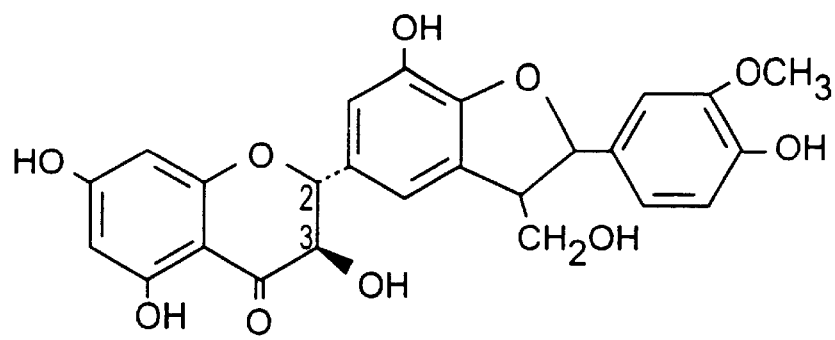
SILYCHRISTIN
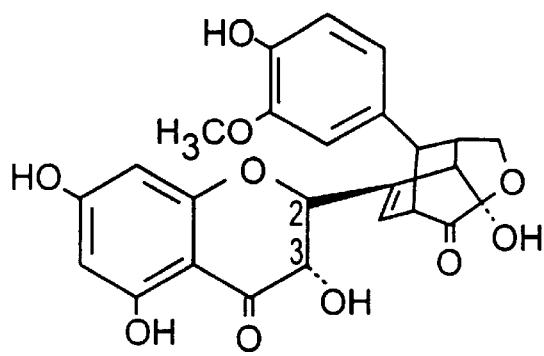
SILYDIANIN
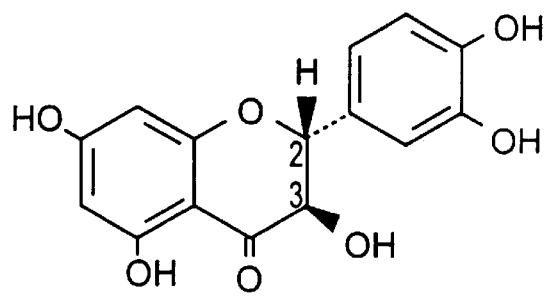
TAXIFOLIN
2,3-DIHYDROQUERCETIN
*FIG. 7*

L-ERGOTHIONEINE, MILK THISTLE, AND S-ADENOSYLMETHIONINE FOR THE PREVENTION, TREATMENT AND REPAIR OF LIVER DAMAGE

In connection with this application, priority is claimed to provisional application, "L-ERGOTHIONEINE, MILK THISTLE, AND S-ADENOSYLMETHIONINE FOR LIVER FAILURE," U.S. Ser. No. 60/076,347, filed Feb. 27, 1998.

FIELD OF THE INVENTION

The present invention relates to compositions for the protection, treatment and repair of liver tissues in humans and animals.

BACKGROUND OF THE INVENTION

The liver is an extremely important organ. As the major metabolic organ of the body, the liver plays some role in almost every biochemical process, including the deamination of amino acids and the formation of urea, the regulation of blood sugar through the formation of glycogen, the production of plasma proteins, the production and secretion of bile, phagocytosis of particulate matter from the splanchnic (intestinal) circulation, and the detoxification and elimination of both endogenous and exogenous toxins.

The many functions of the liver depend on its intimate association with circulating blood. Each liver cell is exposed on at least one face to a blood sinusoid which contains oxygenated arterial blood mixed with venous blood from the splanchnic circulation. This profuse blood supply is necessary for the liver to function. The blood from the sinusoids supplies the hepatocytes with oxygen and nutrients. The hepatocytes use the nutrients both for their own metabolic needs and for the synthesis of the liver's many essential products. Abnormalities in the blood or vasculature can have immediate and severe effects on the liver. For example, liver cells are exposed to high concentrations of any toxic compounds that are ingested orally, such as ethyl alcohol. Even when the ingested compound is not itself toxic, intermediate derivatives produced during hepatic metabolism of the compound may damage the hepatocytes. This phenomenon occurs, for example, in carbon tetrachloride poisoning. Since the blood moves slowly through hepatic sinusoids, liver cells are also quite vulnerable to blood-borne infectious agents such as viruses and bacteria. Furthermore, derangements in hepatic blood pressure can damage liver tissue. Right-sided cardiac failure increases hepatic blood pressure and can lead to pressure necrosis (hepatocellular death) and fibrosis. Left-sided cardiac failure can reduce hepatic perfusion and lead to hepatocellular anoxia and death.

Liver damage from any source may result in liver regeneration, necrosis (cell death), degeneration, inflammation, fibrosis, or mixtures of these processes, depending on the type and extent of injury and its location within the liver. The liver has great functional reserves, but with progressive injury, disruption of liver function can have life-threatening consequences. Cirrhosis, which is a type of end-stage liver disease, is one of the top ten causes of death in the Western world.

Despite the significance and potential severity of liver disease, therapeutic approaches are limited. Treatment is generally symptomatic, e.g., the use of diuretics to combat tissue edema caused by low levels of plasma proteins. Many types of liver disease are the result of viruses (e.g., hepatitis A, B, C, D and E, to name a few), and effective antiviral therapies are rare and commonly cause potentially severe side effects. Other liver diseases are the result of previous toxic exposure (such as alcoholic cirrhosis and exposure to toxic plants, or environmental pollutants) which may be difficult to control. In still other cases, liver disease is the result of poorly understood interplay of various factors, including genetic factors, environmental conditions, and immune system activity (autoimmune hepatitis). These cases are, in a word, idiopathic, and as such are difficult to treat except symptomatically. In short, due in part to the complexity of liver disease, therapies do not currently exist that address its causes. Nor does there currently exist a therapy that supports normal liver function and helps heal damaged liver tissue. Currently available therapies either focus only on the secondary symptoms of liver disease or have significant side effects, as is the case with antiviral drugs. There is a need for a therapeutic composition that will support liver structure, function and healing, with few or no side effects.

SUMMARY OF THE INVENTION

It is a primary object of the present invention to provide compositions for the protection, treatment and repair of liver tissue in humans and animals.

It is a further primary object of the present invention to provide such compositions that also produce a low level of side effects.

It is a further primary object of the present invention to provide a method of using the novel compositions of the present invention to protect, treat or repair liver tissue in humans or animals in need thereof.

The present invention provides novel compositions and methods for protecting, treating and repairing liver tissue. The compositions of the invention include two or more of the following compounds: S-adenosylmethionine, L-ergothioneine and a compound selected from the group consisting of milk thistle, silymarin and active components of silymarin, whether naturally, synthetically, or semi-synthetically derived.

BRIEF DESCRIPTION OF THE DRAWINGS

FIG. 3 diagrams the effects of ethanol in the hepatocyte.

FIG. 7 is the molecular structures of silybin and other compounds from Milk thistle.

DETAILED DESCRIPTION OF THE INVENTION

In accordance with the teachings of the present invention, disclosed herein are compositions and methods for the protection, treatment and repair of liver tissue. The invention relates to novel compositions comprising two or more compounds selected from the group consisting of S-adenosylrnethionine, L-ergothioneine, and a compound selected from the group consisting of Milk thistle (*Silybtim*

*marianum*), silymarin and active components of silymarin, whether naturally, synthetically, or semi-synthetically derived, and to methods of preventing and treating liver disease and of repairing damaged liver tissue.

Figure 1:
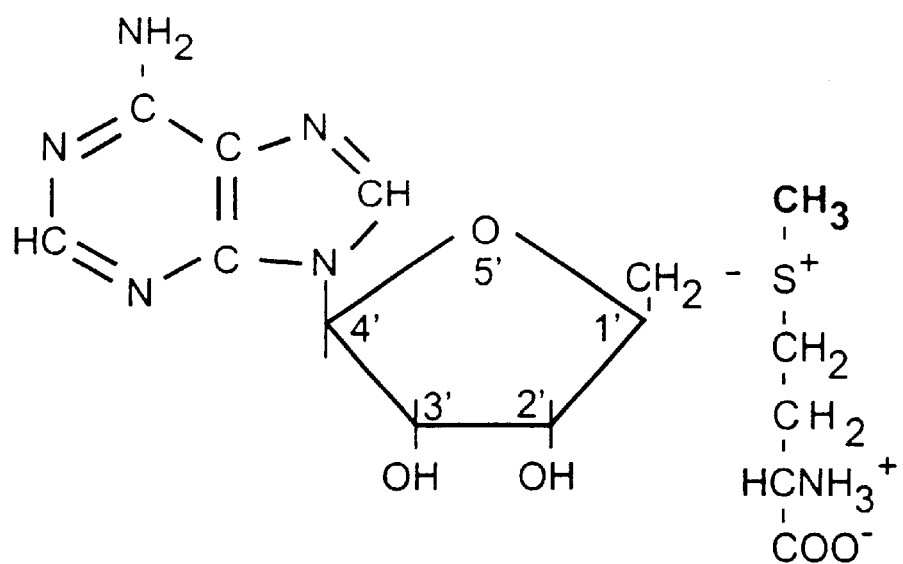
FIG. 1 is the molecular structure of S-adenosylmethionine.
Figure 2:
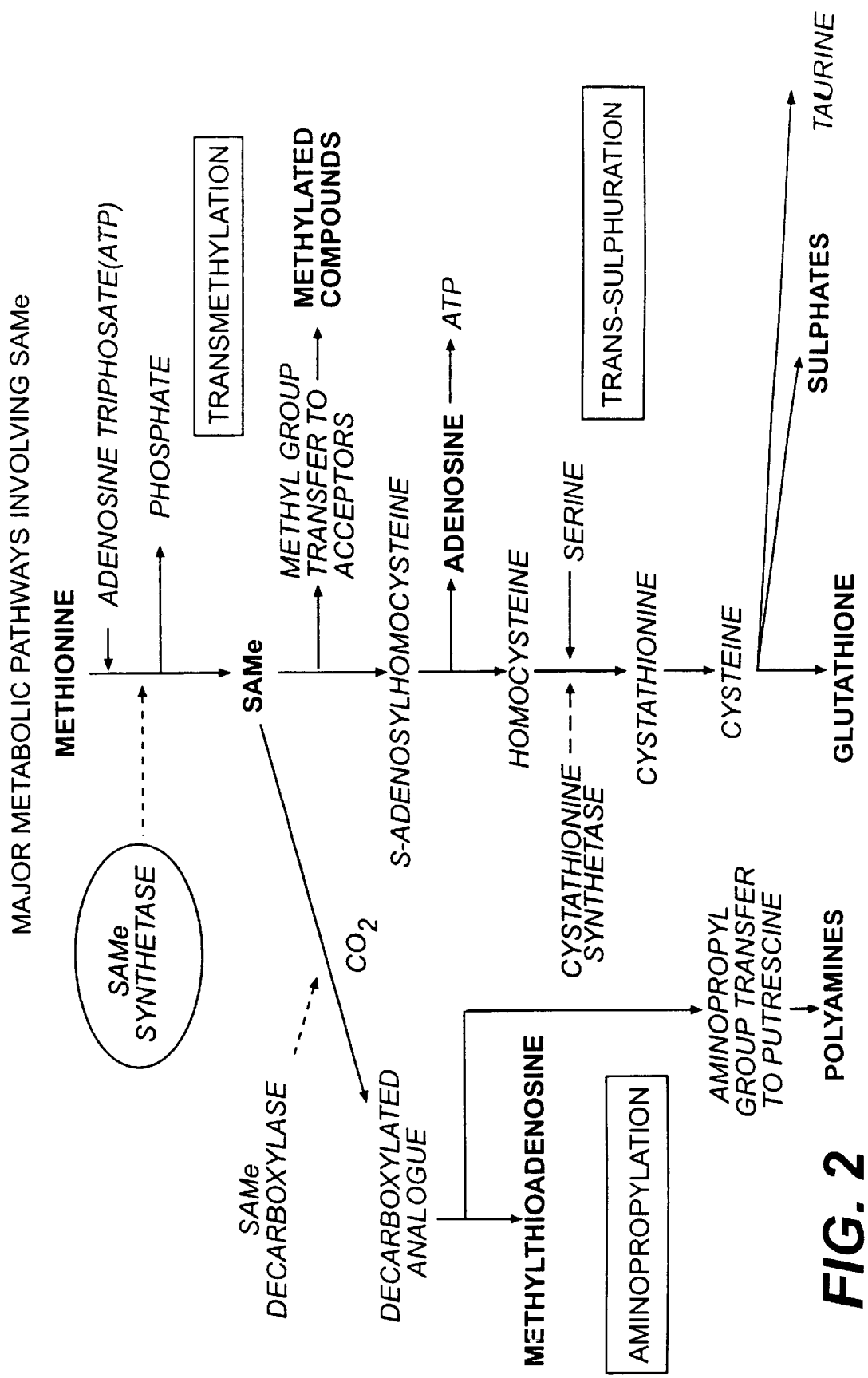
FIG. 2 diagrams the major metabolic pathways of S-adenosylmethionine in the body.

S-adenosylmethionine ("SAMe") (FIG. 1) is a significant physiologic compound that is present throughout body tissue and that takes part in a number of biologic reactions as a methyl group donor or an enzymatic activator during the synthesis and metabolism of hormones, neurotransmitters, nucleic acids, phospholipids, and proteins. It is naturally formed in the body from ATP and methionine. SAMe is an extremely important reactant in many biochemical reactions including transmethylation, transsulfation, and synthesis of aminies (FIG. 2). Stramentinoli, G., Pharmacologic Aspects of S-Adenovylmethionine, American Journal of Medicine 83 (5A), 1987, pp. 35–42. In higher organisms, SAMe plays a silgnificant role in transmethylation processes in more than 40 anabolic or catabolic reactions involving the transfer of the methyl group of SAMe to substrates such as nucleic acids, proteins and lipids, among others. The release of the methyl group from SAMe is also the start of a "transsulfuration" pathway that produces all endogenous sulfur compounds. After donating its methyl group, SAMe is converted into S-adenosylhomocysteine, which in turn is hydrolyzed to adenosine and homocysteine. The amino acid cysteine may then be produced from the homocysteine. Cysteine may exert a reducing effect by itself or as an active part of glutatlhione, which is a main cell antioxidant. Id. SAMe additionally has anti-oxidant effects via its derivatives (e.g., methylthioadenosine), which prevent oxidative damage to cells. Glutathione itself is a product of SAMe via the transmethylation and transsulfation pathways.

SAMe and its products, including glutathione, are of great importance in the prevention of liver damage. The changes produced by ethanol in the liver provide examples of injuries that can occur in the liver on the cellular level (FIG. 3), and help explain the mechanism of action by which SAMe counteracts these injuries.

EtOH absorbed in the blood stream is metabolized in the liver by the enzyme alcohol dehydrogenase. This reaction releases excess nicotinamide-adenine-dinucleotide (NADH) which in turn shunts substrates (carbohydrates, lipids, and proteins) in the liver away from normal catabolic processes and towards lipid biosynthesis. As lipids accumulate in the liver cells in the form of large droplets, organelles are physically displaced and crowded, and this phenomenon decreases the cells' ability to function. Secondly, alcohol induces the P 450 system of cytochromes, and the microsomal ethanol oxidizing system ("MEOS") within liver cells, leading to augmented transformation of various compounds in the body (including, for example, chemicals from tobacco smoke) into toxic metabolites, and producing free radicals. Because alcohol consumption decreases glutathione pools, damage already produced by these free radicals is exacerbated. Alcohol and its metabolites (e.g., acetaldehyde) also interact with phospllolipids and therefore have direct effects on hepatocellular membranes, decreasing their fluidity and affecting the function of organelles such as mitochondria and endoplasmic reticulum. Finally, acetaldehyde alters hepatocellular proteins, including the sodium/potassium pump, decreasing the ability of these proteins to function. The sodium/potassium pump is a membrane-bound protein that is responsible for maintaining the balance of sodium and potassium across the cell membrane of every cell in the body. Because many cell functions depend on the electrochemical gradient that results from this distribution of sodium and potassium, the sodiun/potassium pump is essential to enable cells to perform. liver cells are no exception. The alterations in proteins that alcohol and its metabolites induce also have the effect of making these proteins more 'foreign' and thus more likely to induce autoimmune reactions. In short, alcohol damages the liver in a myriad of ways. FIG. 3; Lieber, C., Biochemical factors in alcoholic liver disease, Seminars in Liver Disease, 13 (2), 1993, pp. 136–53.

SAMe has a variety of beneficial effects in cells and protects hepatocytes from these injurious influences in a number of different ways. For example, SAMe has been shown to decrease lipid accumulation in rats chronically intoxicated with ethanol. This effect is not completely understood, but is partially explained by SAMe's ability to inhibit alcohol dehydrogenase. This single function of SAMe in itself prevents not only lipid accumulation but also much of the additional damage acetaldehyde causes to cellular membranes and proteins. Pascale. R., et al., Inhibition by ethanol of rat liver plasma membrane (Na+K+) ATPase: protective effect of SAMe, L-methionine, and N-acetytlcysteine, Toxicology and Applied Pharmacology, 97, 1989, pp. 216–29. Furthermore, because SAMe catalyses the transformation of phosphatidylethanolamine to phosphatidylcholine, it supports the normal fluidity of cell membranes, thereby supporting the structure and function of organelles including the plasma membrane, mitochondria and endoplasmic reticulum. This supportive effect avoids many of alcohol's damaging secondary effects. Bevi B., et al., Protection of rat fetal hepatocytes membranes from ethanol medicated cell injury and growth impairment, Hepatology 16, 1992, p. 109 A.

SAMe also protects liver cells indirectly via its antioxidant products cysteine and glutathione, which help prevent damage by the excessive free radicals produced during alcohol intoxication. Pascale R., et al., The role of SAMe in the regulation of glutathione pool and acetaldehyde production in acute ethanol intoxication, Research Communications in Substances of Abuse, Vol. 5, No. 4, 1984, pp. 321–24.

Laboratory animal studies and in vitro experiments have verified these effects of SAMe on the inner, lipid layer of the plasma membrane. Champ, P. and Harvey, R., Biochemistry, $2^{nd}$ ed., Lippincott, Pa., 1994, pp. 266–7; Stramentinoli, G., Pharmacologic aspects of, SAMe, American Journal of Medicine, Vol. 83 (5A) 1987, p. 35; Baldessarini, F., Neuropharmacology of S-Adenosyl Methionine, American Journal of Medicine 83 (5A), 1987, p. 95; Carney, M., Neuropharmacology of S-Adenosyl Methionine, Clinical Neuropharmacology 9 (3), 1986, p. 235; Janicak, P., S-Adenosylmethionine in Depression, Alabama Journal of Medical Sciences 25 (3), 1988, p. 306.

SAMe has been used to treat various disorders. In certain forms of liver disease, SAMe acts as an anticholestatic agent. Adachi, Y., et al., The Effects of S-adenosylrnethionine on Intrahepatic Cholestasis, Japan Arch. Inter. Med., 33 (6), 1986, pp. 185–92. One mechanism by which SAMe exerts this effect is via its ability to maximize membrane fluidity, which is a crucial factor in the secretion of bile acids from hepatocytes. Id. Another mechanism is via the transsulfation pathway and the production of sulfates and taurine, which are important in mobilization of bile acids. Frezza, M., The use of SAMe in the treatment of cholestatic disorders, Drug Investigation, 4 (Suppl. 4), 1992, pp. 101–08. Low levels of SAMe are believed to play a role in increasing the risk of certain cancers. Feo F., et al., Early Stimulation of Polyamine Biosynthesis During Promotion by Phenobarbital of Diethylenetriamine-induced Rat Liver Carcinogenesis. The Effects of Variations of the S-adenosyl-L-methionine Cellular Pool, Carcinogenesis, 6 (12), 1985, pp. 1713–20. The administration of SAMe has also been associated with a fall in the amount of early reversible nodules and the prevention of the development of late pre-neoplastic lesions and hepatocellular carcinomas. Garcea, R., et al., Variations of Ornithine Decarboxylase Activity and S-adenosyl-L-methionine and 5'-methylthioadenosine Contents During the Development of Diethylenetriamine-induced Liver Hyperplastic Nodules and Hepatocellular Carcinoma, Carcinogenesis, 8 (5), 1987, pp. 653–58.

Figure 4:
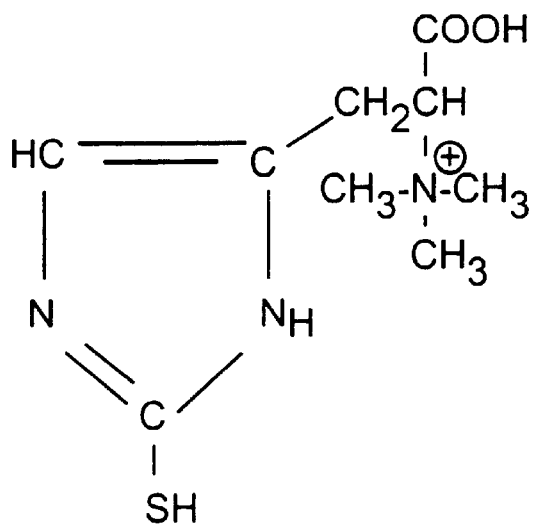
FIG. 4 is the molecular structure of L-ergothioneine.
Figure 5:
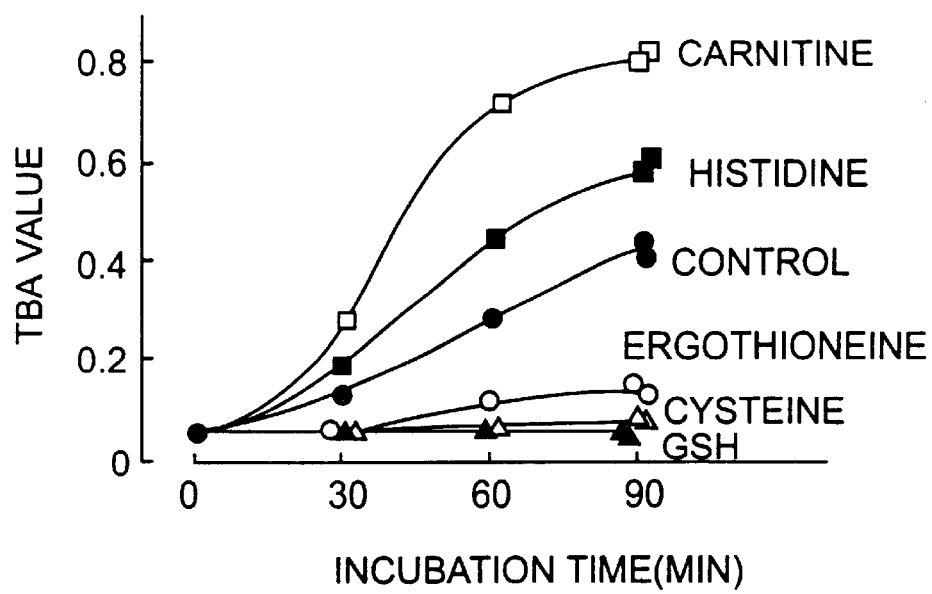
FIG. 5 shows the effect of ergothioneine and other compounds on lipid peroxide formation in mouse liver homogenate.

L-ergothioneine (FIG. 4) is a naturally occurring antioxidant that is very stable in the body. It is synthesized in fungi and microorganisms and present in both plants and animals. Animals are unable to synthesize L-ergothioneine and must obtain it from dietary sources. It is readily absorbed and is active in most mammalian tissues, concentrating especially in the liver, where it prevents certain types of free-radical-induced damage to cell membranes and organdies. For example, exogenous L-ergothioneine has been shown to prevent lipid peroxidation by toxic compounds in the liver tissue of rats. Akanmu, D., et al., The cantioxidant action of ergothioneine, Arch. of Biochemistry and Biophysics, 288 (1), 1991, pp. 10–16; Kawano, H., et al., Studies on Ergothioneine. Inhibitory effect on lipid peroxide formation in mouse liver, Chem. Pharm. Bull., 31 (5), 1983, pp. 1662–87. In a study comparing the inhibition of lipid peroxide ("LPO") formation by various compounds in mouse liver, L-ergothioneine both inhibited LPO formation and enhanced the decomposition of existing LPO (FIG. 5). Id. L-ergothioneine additionally has been shown to inhibit the damaging effects caused by the oxidation of iron-containing compounds such as hemoglobin and myoglobin. These molecules are important in the body as carriers of oxygen, but because they contain divalent iron, they can interact with hydrogen peroxide via the Fenton reaction to produce the even more damaging hydroxyl radical. This is the mechanism by which damage occurs during so-called reperfusion injury. Because L-ergothioneine acts as a reducing agent of the ferryl-myoglobin molecule, it can protect tissues from reperfusion injury. Hanlon, D., Interaction of ergothioneine with metal ions and metalloenzymes, J. Med. Chem., 14 (11), 1971, pp. 1084–87. Although L-ergothioneine does not directly scavenge superoxide anion or hydrogen peroxide, it contributes to the control of these free radicals by participating in the activation of superoxide dismutase and glutathione peroxidase. Its protective effects on cell membranes and other organelles are of benefit in acute and chronic toxicity as well as in infectious diseases, because common pathogenic biomechanisms are active in both of these processes.

Figure 6:
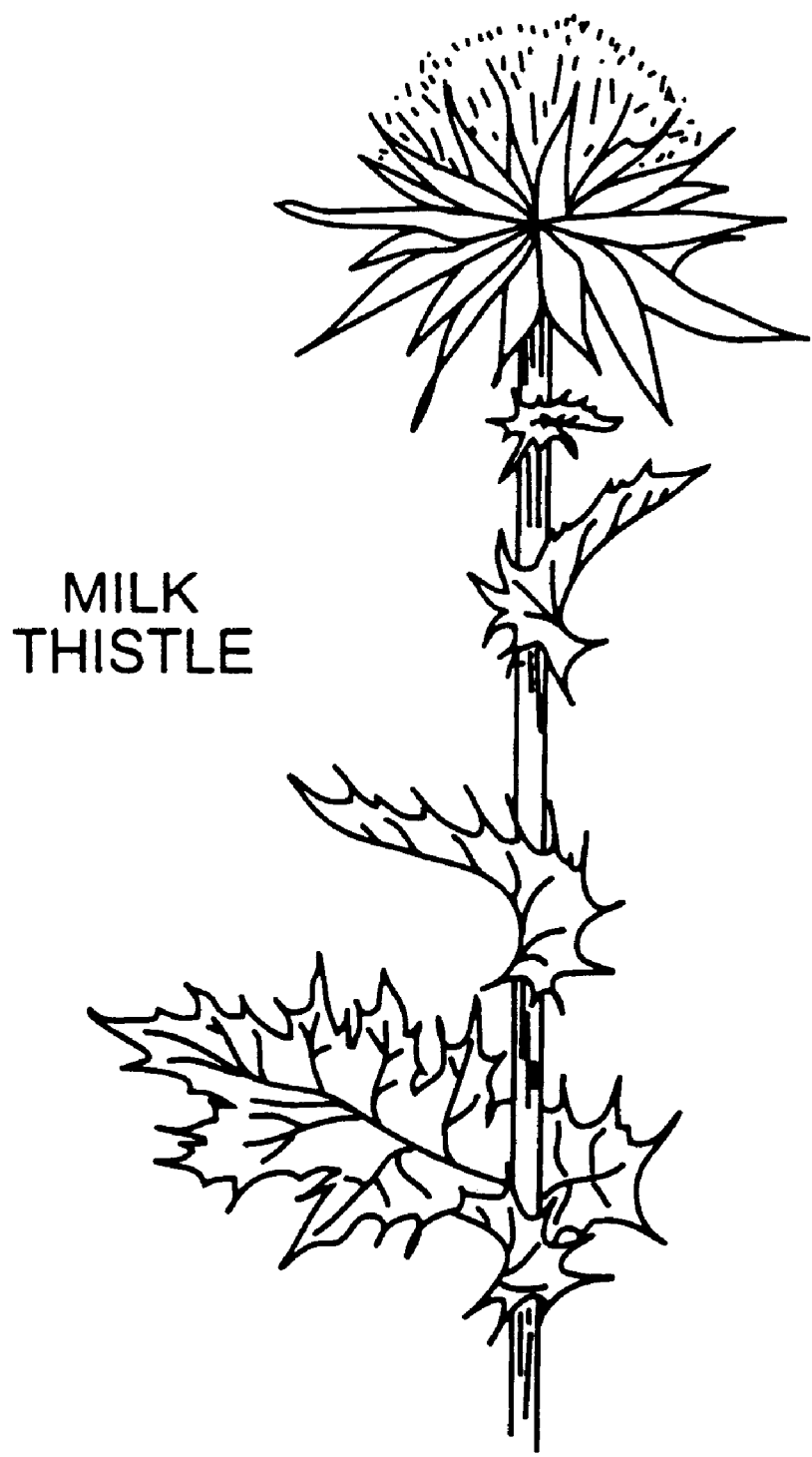
FIG. 6 is a drawing of the herb Milk thistle (*Silybum marianun*).

Milk thistle (*Silybum marianum*) (FIG. 6), which is also commonly known as Marian thistle, St. Mary's thistle, and Our Lady's thistle, is a native to the Mediterranean regions, but has been naturalized in California and the eastern United States. This tall herb with prickly variegated leaves and milky sap has been used as a folk remedy for liver and biliary complaints for many years and recent research has supported such medicinal use. Foster. S., A Field Guide to Medicinal Plants, Houghton Mifflin Co, Boston, 1990, p. 198.

Research over the past 20 years has documented that the plant contains a compound referred to as silymarin, which actually consists of various forms of hepatoprotectant flavonolignans including silybin, isosilybin, dehydrosilybin, and others. (FIG. 7). Tyler, V., The Honest Herbal, Haworth Press, Inc., New York, 1993, pp. 209–10; Wichtl, M. (Girainger Bisset, N, trans.), Herbal Drugs and Phytopharmaceuticals, CRC Press, Boca Raton 1994, pp. 121, 124, 125. These hepatoprotectant flavonolignans are referred to in this application as "active components of silymarin." The fruits (often erroneously referred to as the "seeds") of the plant, for example, contain approximately 3% flavonolignans on average. Laboratory trials in animals have shown that silymarins protect liver tissue against a variety of toxins including those of the deadly amanita mushrooms and carbon tetrachloride. Prophylactic effects were especially pronounced. Milk thistle is usually available as an extract that contains silymarin, but it is envisioned that any form or formulation of milk thistle, e.g., extract, precipitate, or powdered form, which contains either silymarin or one or more active components of silymarin, would function in the present invention.

Silymarin and the active components of silymarin have several mechanisms of action, including stimulation of nucleolar polymerase A. This stimulation in turn increases ribosomal activity leading to increased synthesis of cellular proteins, and an increased rate of hepatocellular repair. Conti, M., et al., Protective activity of Silipide on liver damage in rodents, Japan J. Pharmacol., 60, 1992, pp. 315–21. Other protective mechanisms involve changes in the molecular structure of the hepatocellular membrane, which reduce binding and entry of toxins into the cell, and an antioxidant effect. Parish, R. & Doering, P., Treatment of Amanita mushroom poisoning: a review, Vet. Hum. Toxocol., 28 (4) 1986, pp. 318–22.

It is expected that elements of the combinations of the present invention will work synergistically together because they have different, but complementary, mechanisms of action. Because liver diseases involve a complex interplay of numerous factors, the exact nature of which may remain obscure to the diagnosing clinician, there is a need for a composition that will address numerous mechanisms of liver damage. Treating the causative agent may not be—and in liver disease rarely is—possible. Addressing and preventing hepatic injuries on the cellular level therefore frequently will be the best treatment possible and almost as beneficial. The present invention combines antiinflammatory, anti-lipid, anti-necrotic, regenerating, and anti-fibrotic effects. All three ingredients that may be included in compositions of the present invention, S-adenosylmethionine, L-ergothioneine and a compound selected from the group consisting of Milk thistle, silymarin and active components of silymarin, have strong anti-inflammatory effects because of their antioxidant properties. Because different antioxidants have their primary effect on different free radicals, (for example, superoxide dismutase scavenges primarily superoxide anion), and because several types of free radicals are implicated in liver damage, supplying just one antioxidant would only address one subset of liver-damaging free radicals. The addition of SAMe with its anti-lipid effects produces additional and complementary benefits because SAMe helps prevent fatty change in liver cells, a pathological change common to many liver diseases. By preventing reperfusion injury, L-ergothioneine prevents cellular death as well as resulting pathologic fibrotic changes in the liver. Finally, the phytocompounds in milk thistle provide regenerative action by stimulating protein synthesis. This action is supported by SAMe, because methylation of DNA and proteins is an essential part of protein synthesis. Combining two of the three compounds will produce a beneficial effect in a number of liver diseases, and combining all three compounds will help treat or prevent an extremely broad range of such diseases. The combination will also allow beneficial effects to be achieved using lower doses than would otherwise be necessary. Tile use of lowered doses is both economically advantageous and reduces the risk of any potential side effects. Although the present ingredients are remarkably free of side effects, no compound is completely innocuous and giving the lowest effective dose is always sound medical policy.

The compositions of the present invention can be administered by a variety of routes including, but not limited to: orally, parenterally, transdermally, sublingually, intravenously, intramuscularly, rectally and subcutaneously. Preferred daily doses for each of the compounds are as follows:

SAMe
- Total dose range: 5 mg–10 grams
- Preferred small animal dose range: 5 mg–10 grams
- Preferred human dose range: 20 mg–5000 mg
- Preferred large animal dose range: 100 mg–10 grams
- Alternatively, the daily per kilogram dose range of SAMe for all species is:
- 2 mg/kg–100 mg/kg L-ergothioneine
- Total dose range: 25 mg–25 grams
- Preferred small animal dose range: 25 mg–5 grams
- Preferred human dose range: 50 mg–10 grams
- Preferred large animal dose range: 100 mg–25 grams Milk Thistle (or silymarin, or active components of silymarin, i.e., silybin, isosilybin, etc.)
- Total dose range: 5 mg–10 grams
- Preferred small animal dose range: 5 mg–1000 mg
- Preferred human dose range: 100 mg–5 grams
- Preferred large animal dose range: 250 mg–10 grams
- Alternatively, the daily per kilogram dose range of Milk thistle, silymarin, or active components of silymarin for all species is:
- 1 mg/kg–200 mg/kg Having discussed the composition of the present invention, it will be more clearly perceived and better understood from the following specific examples which are intended to provide examples of the preferred embodiments and do not limit the present invention. Moreover, as stated above, the preferred components described in these examples may be replaced by or supplemented with the any of the components of the compositions of the invention described above.

EXAMPLE 1

A 10-year-old female spayed domestic cat is diagnosed with feline idiopathic hepatic lipidosis (fatty liver). This disease is characterized by the accumulation of triglycerides within the cytoplasm of liver cells. The cells become so swollen with lipids that they cease to function, and many die (hepatic necrosis). The cellular swelling also inhibits blood flow in hepatic sinusoids, compounding the damage with poor perfusion. Symptoms of the disease include loss of appetite, vomiting, depression and CNS signs (hepatic encephalopathy). Since the cause of this disease is unknown, it is currently treated symptomatically. Even with aggressive treatment, 40 to 50% of affected animals succumb. In this case, in addition to symptomatic treatment (tube feeding, fluids, pharmacologic control of vomiting), the patient is given daily a mixture of 100 mg SAMe, 100 mg silymarin, and 100 mg of L-ergothioneine until appetite returns. The SAMe and silymarin support repair of damaged hepatocytes and their function, the production of enzymes and other proteins. The L-ergothioneine prevents reperfusion injury. The net result is that the cat recovers, and the rate of recovery is increased so that the cat spends fewer days hospitalized.

EXAMPLE 2

A farmer in Lancaster County, Pennsylvania, reports that one of his cows has died in convulsions and that several sheep and a pig in the same pasture are also sick. Poisoning by cocklebur plants (*Xanthium strumarium*) is diagnosed. In this condition, a toxin produced by the plant causes fatty change, swelling, and death in liver cells. Animals that survive the initial illness may develop chronic liver disease. Currently, the oily method of treatment is removal of the plant from the diet. In this case, the pigs and sheep are removed from the pasture and administered daily a combination of SAMe (5 mg/kg), silymarin (40 mg/kg), and L-ergothioneine (100 mg per animal) for one to two weeks. The SAMe helps maintain cellular membranes and the Na/K/ATPase pump, which are the cellular organelles most likely to be damaged by the toxin. The silymarin stimulates synthesis of replacement proteins and the L-ergothioneine prevents reperfusion injury.

EXAMPLE 3

A 58-year-old man has osteoarthritis. To control the pain in his joints, he takes large amounts of the drug acetaminophen. Like many other drugs, acetaminophen can cause hepatic damage by decreasing glutathione levels. This patient wishes to continue to take acetaminophen, because nonsteroidal anti-inflammatory drugs cause unacceptable gastrointestinal irritation. In this case, the patient continues to take acetaminophen, but also takes SAMe 200 mg, and L-ergothioneine 100 mg daily as long as he continues to take acetaminophen. The SAMe increases hepatic glutathione levels, and the L-ergothioneine ensures maximum effect of the available glutathione via glutathione peroxidase activation. The net result is that liver structure and function are supported in the face of an ongoing potentially hepatotoxic exposure.

Many modifications may be made without departing from the basic spirit of the present invention. Accordingly, it will be appreciated by those skilled in the art that within the scope of the appended claims, the invention may be practiced other than has been specifically described herein. Hence, the attached claims are intended to cover the invention embodied in the claims and substantial equivalents thereto.

What is claimed is:
1. A composition comprising:
   a. S-adenosylmethionine and
   b. L-ergothioneine.
2. A composition comprising:
   a. S-adenosylmethionine and
   b. one or more substances selected from the group consisting of a constituent of Milk thistle (*Silybum marianum*), silymarin and active components of silymarin.
3. A method of improving or maintaining the health of liver tissue of a human or other animal comprising administering to the human or animal a therapeutically or prophylactically effective amount of the composition of claim 1.
4. A method of normalizing or improving the function of the liver of a human or other animal comprising adminis- tering to the human or animal a therapeutically or prophylactically effective amount of the composition of claim 1.

5. A method of improving or maintaining the health of liver tissue of a human or other animal comprising administering to the human or animal a therapeutically or prophylactically effective amount of the composition of claim 2.

6. A method of normalizing or improving the function of the liver of a human or other animal comprising administering to the human or animal a therapeutically or prophylactically effective amount of the composition of claim 2.

7. The method of claims 3, 4, 5 or 6 in which a daily dose of S-adenosylmethionine for humans or animals ranges from 5 milligrams to 10 grams.

8. The method of claims 3, 4, 5 or 6 in which a daily dose of S-adenosylmethionine for humans or animals ranges from 2 milligrams per kilogram to 100 milligrams per kilogram.

9. The method of claims 3 or 4 in which a daily dose of L-ergothionenine for humans or animals ranges from 25 milligrams to 25 grams.

10. The method of claims 5 or 6 in which a daily dose of the substance from the group consisting of a constituent of Milk thistle (*Silybum marianum*), silymarin and active components of silymarin for humans or animals ranges from 5 milligrams to 10 grams.

11. The method of claims 5 or 6 in which the daily dose of the substance selected from the group consisting of a constituent of Milk thistle (*Silybum marianum*), silymarin and active components of silymarin for humans or animals ranges from 1 milligrams per kilogram to 200 milligrams per kilogram.

12. The method of claims 4, 5, 7 or 9 in which a daily dose of L-ergothioneine for humans or animals ranges from 25 milligrams to 25 grams.

13. The method of claims 6, 7, 8 or 9 in which a daily dose of the substance selected from the group consisting of a constituent of Milk thistle (*Silybum marianum*), silymarin and active components of silymarin for humans or animals ranges from 5 milligrams to 10 grams.

14. The composition of claim 1 in which a single dose of L-ergothionenine for humans or animals ranges from 25 milligrams to 25 grams.

15. The composition of claim 2 in which a single dose of the substance selected from the group consisting of a constituent of Milk thistle (*Silybum marianum*), silymarin and active components of silymarin for humans or animals ranges from 5 milligrams to 10 grams.

16. The composition of claim 2 in which a single dose of the substance selected from the group consisting of a constituent Milk thistle (*Silybum marianum*), silymarin and active components of silymarin for humans or animals ranges from 1 millgram per kilogram to 200 milligrams per kilogram.

* * * * *